US010663367B2

(12) United States Patent
Dittberner et al.

(10) Patent No.: US 10,663,367 B2
(45) Date of Patent: May 26, 2020

(54) ADAPTIVE SENSING FOR A GAS LEAK DETECTION

(71) Applicant: INTERNATIONAL BUSINESS MACHINES CORPORATION, Armonk, NY (US)

(72) Inventors: Matthias Dittberner, Yorktown Heights, NY (US); Levente Klein, Tuckahoe, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 368 days.

(21) Appl. No.: 15/662,730

(22) Filed: Jul. 28, 2017

(65) Prior Publication Data

US 2019/0033160 A1    Jan. 31, 2019

(51) Int. Cl.
*G01M 3/16*     (2006.01)
*G01M 3/18*     (2006.01)
(Continued)

(52) U.S. Cl.
CPC ........... *G01M 3/16* (2013.01); *G01M 3/18* (2013.01); *G01N 27/04* (2013.01); *G01N 27/045* (2013.01);
(Continued)

(58) Field of Classification Search
CPC .. G01N 27/04; G01N 27/045; G01N 33/0031; G01N 33/0034; G01N 33/0004;
(Continued)

(56) References Cited

U.S. PATENT DOCUMENTS

| 5,297,421 A * | 3/1994 | Hosonuma | ............ G01P 13/02 |
| | | | 73/31.02 |
| 2008/0183389 A1 * | 7/2008 | Chainer | ............ G01W 1/00 |
| | | | 702/2 |
| 2011/0295575 A1 | 12/2011 | Levine et al. | |

FOREIGN PATENT DOCUMENTS

| CN | 101350828 A | 1/2009 |
| CN | 103914622 A | 7/2014 |
| | (Continued) | |

OTHER PUBLICATIONS

The International Search Report and the Written Opinion of the International Searching Authority, or the Declaration, International Application No. PCT/IB2018/054362, dated Oct. 10, 2018, International filing date Jun. 14, 2018, 9 pages.
(Continued)

*Primary Examiner* — Robert R Raevis
(74) *Attorney, Agent, or Firm* — Cantor Colburn LLP; Vazken Alexanian (57) ABSTRACT

A method, a system and an apparatus for adaptively sensing a gas leak. The method includes: obtaining wind data from a wind sensor, identifying at least one wireless mote in a plurality of wireless motes that is most likely to detect a gas plume from the wind data, activating the identified at least one wireless mote to trigger measuring gas concentration of the gas plume, and identifying the location of the gas leak if the gas concentration is above a predetermined threshold. Also included is a system for adaptively sensing a gas leak having a wind sensor, a plurality of wireless motes and a server in communication therewith. An apparatus for adaptively sensing a gas leak in an industrial site is also provided.

15 Claims, 6 Drawing Sheets

(51) Int. Cl.
*G01N 27/04* (2006.01)
*G01N 33/00* (2006.01)
*G01W 1/00* (2006.01)

(52) U.S. Cl.
CPC .......... *G01N 33/0031* (2013.01); *G01W 1/00* (2013.01); *G01W 2001/003* (2013.01)

(58) Field of Classification Search
CPC ..... G01N 33/0036–0054; G01W 1/00; G01W 2001/003
USPC ......... 73/31.02, 31.03, 865.8, 432.1; 700/90, 700/67, 69, 73, 74; 166/336, 337, 166/250.01, 250.08, 250.16; 340/605
See application file for complete search history.

(56) References Cited

FOREIGN PATENT DOCUMENTS

| CN | 104253867 A | 12/2014 |
|---|---|---|
| CN | 104834017 A | 8/2015 |
| CN | 104101686 B | 9/2015 |
| CN | 105372388 A | 3/2016 |
| CN | 105510535 A | 4/2016 |
| CN | 103196038 A | 8/2016 |

OTHER PUBLICATIONS

Fedorenko, George, "Semiconductor Gas Sensors Based on Pd/SnO2 Nanomaterials for Methane Detection in Air", Nanoscale Res Lett., Published Online May 4, 2017 <https://www.ncbi.nlm.nih.gov/pmc/articles/PMC5418166//>.

Venkatram, Akula, "Modeling dispersion at distances of meters from urban sources", Atmospheric Environment, Sep. 2004, pp. 4633-4641, vol. 38—Iss. 28, Elsevier <http://www.sciencedirect.com/science/article/pii/S1352231004004947/>.

Qian, Wenjun, "Performance of Steady-State Dispersion Models Under Low Wind-Speed Conditions", Boundary-Layer Meteorology, Mar. 2011, pp. 475-491, vol. 138—Iss. 3, Springer, Published Online <https://rd.springer.com/article/10.1007%2Fs10546-010-9565-1?LI=true/>.

Unkown, "Briggs plume rise equation", Environmental Information System, Published Online <http://www.envis.org/technology/air-pollution/951-briggs-plume-rise-equation/>.

* cited by examiner

ADAPTIVE SENSING FOR A GAS LEAK DETECTION

STATEMENT REGARDING FEDERALLY SPONSORED WORK

This invention was made with United States support under contract number DE-AR0000540 entered with the following United States Governmental Agency: Department of Energy. The United States government has certain right to this invention.

TECHNICAL FIELD OF THE INVENTION

The present invention relates generally to the field of gas leak detection and, more particularly, to a method and system for adaptive sensing for gas leak detection.

BACKGROUND OF THE INVENTION

A gas leak refers to a leak of natural gas or other gaseous product from a pipeline or other containment into any area where the gas should not be present. Because a small leak may gradually build up an explosive concentration of gas, leaks are very dangerous. In addition to causing fire and explosion hazards, leaks can have a harmful impact on human health, kill vegetation, including large trees, and may release powerful greenhouse gases to the atmosphere. The primary purpose of leak detection systems (LDS) is to help pipeline controllers to detect and localize leaks. LDS provide alarms and display other related data to the pipeline controllers to assist decision-making. Pipeline leak detection systems can also enhance productivity and system reliability thanks to reduced downtime and inspection time.

Currently, any given wireless sensor network for detecting gas leaks require measurements from all sensors in the network and transmit all measured sensor data to a central server, which requires high bandwidth communications and large storage capacity to store historical data. The continuous operation of sensors require adequate power to operate the sensors that can be a burden on batteries. The acquired data are analyzed on a central server using statistical methods to determine the frequency of events across a time interval and establish plume levels and locations. However, more than 70% of the information transmitted back to the central server contain little or no values as the sensors are not exposed to a gas plume causing analytics to fail. The methods known in the art cannot offer a real-time assessment of gas leaks and often require massive data collection.

SUMMARY OF THE INVENTION

According to an embodiment of the present invention, a method of adaptively sensing a gas leak is provided. The method includes: obtaining wind data from a wind sensor, identifying at least one wireless mote in a plurality of wireless motes that is most likely to detect a gas plume from the wind data, activating the identified at least one wireless mote to trigger measuring gas concentration of the gas plume, and identifying the location of the gas leak if the gas concentration is above a predetermined threshold.

According to an embodiment of the present invention, a system for adaptively sensing a gas leak is provided. The system includes: a wind sensor located on a gas extraction well pad, wherein the wind sensor is configured to obtain wind data by sensing wind speed and wind direction, a plurality of wireless motes located in proximity of the wind sensor, wherein each wireless mote is configured to detect the presence of gas; and a server located in proximity of the gas extraction well pad, wherein the server is configured to communicate with the plurality of wireless motes and the wind sensor.

According to an embodiment of the present invention, an apparatus for adaptively sensing a gas leak in an industrial site is provided. The apparatus includes: a plurality of gas extraction well pads contained in the industrial site, a plurality of wind sensors each located in the proximity of each gas extraction well pad, wherein each wind sensor is configured to obtain wind data by sensing wind speed and wind direction, a plurality of wireless motes located in the proximity of each gas extraction well pad and a wind sensor in plurality of wind sensors, wherein each wireless mote is configured to detect the presence of gas, and a server located in proximity of the industrial site, wherein the server is configured to communicate with the plurality of wireless motes and the plurality of wind sensors.

DETAILED DESCRIPTION OF THE PREFERRED EMBODIMENTS

Some preferred embodiments will be described in more detail with reference to the accompanying drawings, in which the preferred embodiments of the present invention have been illustrated. However, the present invention can be implemented in various manners, and thus should not be construed to be limited to the embodiments disclosed herein. On the contrary, those embodiments are provided for the thorough and complete understanding of the present invention, and to completely convey the scope of the present invention to those skilled in the art.

Embodiments of the present invention recognize that gas plumes created by small leaks may not be well defined spatially and temporally in their close proximity as the gas plume changes shape and extension in response to wind speed and direction. Also, while current models of Gaussian plumes are valid at large distances from the source of the gas leak, these models are not suitable in close proximity to the source of the gas leak. Consequently, any gas concentration measurement close to a gas leak requires correlation between the wind direction and gas level measured. Furthermore, current methods of detection using wireless sensor networks require obtaining measurement data from all of the sensors in the network at fixed intervals, which may not sample the gas plume at the best moment and result in a large amount of acquired data.

Embodiments of the present invention provide a method and system for controlling the data acquisition moment and the number of acquired data points to reduce the number of sensors in the network that need to actively sample the environment. Subsequently, the accuracy of gas plume detection is increased and the number of acquired data points is decreased.

More specifically, the present invention provides a method of adaptively sensing a gas leak. The method includes obtaining wind data from a wind sensor. The wind data includes both wind speed and wind direction. The wind data can then be used to identify at least one wireless mote in a plurality of wireless motes that is most likely to detect a gas plume from the wind data. The method then activates the identified at least one wireless mote to trigger measuring gas concentration of the gas plume and identifies the location of the gas leak if the gas concentration is above a predetermined threshold.

Furthermore, if the gas concentration of the plume is below the predetermined threshold, the method proceeds to obtain wind data from the wind sensor a second time. Then, identifies a second at least one wireless mote in the plurality of wireless motes that is most likely to detect the gas plume from the wind data. The second identified at least one wireless mote is then triggered to begin measuring gas concentration of the gas plume and the location of the gas leak is identified if the gas concentration is above the predetermined threshold.

In addition, identifying the at least one wireless mote in the plurality of wireless motes that is in a path of the gas plume can be done using a wind turbulence value and a gas plume dissipation rate. This may require determining a gas plume dispersion pattern from the wind data.

In various embodiments of the present invention, measuring gas concentration at the identified at least one wireless mote most likely to detect the gas plume may be performed in a variety of ways. For instance, gas concentration can be measured more frequently than the remaining wireless motes.

Alternatively, a well-defined moment of time can be calculated from the wind turbulence value and the gas plume dispersion pattern when the gas plume is expected to pass near the identified at least one wireless mote most likely to detect the gas plume. Then, measuring gas concentration can be triggered at the well-defined moment of time.

Also, if a location of a gas leak is identified, then a distance between the identified at least one wireless more most likely to detect the gas plume and the location of the gas leak can be calculated and measuring gas concentration can be triggered at an interval proportional to a gas plume concentration and the distance.

A method of the present invention also provides for excluding the remaining wireless motes in the plurality of wireless motes from taking measurements to conserve power and data communication bandwidth.

In addition, the present invention can identify a gas type, calculate an escape rate of the gas plume from the gas leak, and determine the chemical composition of the gas plume.

The present invention also provides a system for adaptively sensing a gas leak. The system includes a wind sensor configured to obtain wind data by sensing wind speed and wind direction located on a gas extraction well pad. Further, the system can have a plurality of wireless motes located in proximity of the wind sensor configured to detect the presence of gas. The system can have a server located in proximity of the gas extraction well pad. The server is configured to communicate with the plurality of wireless motes and the wind sensor.

In addition, the server may determine a gas plume dispersion pattern from the wind data. The server can be further configured to calculate a wind turbulence value from the wind data, calculate a gas plume dissipation rate from the wind turbulence value, and identify at least one wireless mote in the plurality of wireless motes that is in a path of a gas plume from the wind turbulence and the gas plume dispersion pattern.

The server may also activate the identified at least one wireless mote in the plurality of wireless motes to take a measurement at (1) an interval more frequent than the remaining wireless motes in the plurality of wireless motes, (2) a well-defined moment of time when the gas plume is expected to pass nearby the at least one wireless mote, wherein the well-defined moment of time is calculated using the wind turbulence value and the gas plume dispersion pattern, or (3) an interval proportional to a gas plume concentration and a distance between the at least one wireless mote in the plurality of wireless motes and the location of the gas leak.

Additionally, the server may exclude at least one wireless mote in the remaining wireless motes in the plurality of wireless motes from taking measurements resulting in less power consumption and a reduced data communication bandwidth.

The server may determine the location of the gas leak from the wind data and the measurement from the at least one wireless mote in the plurality of wireless motes. The escape rate of the gas plume from the gas leak and the chemical composition of the gas plume can also be determined.

Embodiments of the present invention also provide an apparatus for adaptively sensing a gas leak in an industrial site. The apparatus includes a plurality of gas extraction well pads contained in the industrial site. A plurality of wind sensors are each located in the proximity of each gas extraction well pad, wherein each wind sensor is configured to obtain wind data by sensing wind speed and wind direction. A plurality of wireless motes are located in the proximity of each gas extraction well pad and a wind sensor in plurality of wind sensors, wherein each wireless mote is configured to detect the presence of gas. Then, a server, located in proximity of the industrial site, is configured to communicate with the plurality of wireless motes and the plurality of wind sensors.

Embodiments of the present invention will now be described in detail with reference to the Figures. Note that all dashed lines in any of the Figures indicate a wireless connection.

Figure 1:
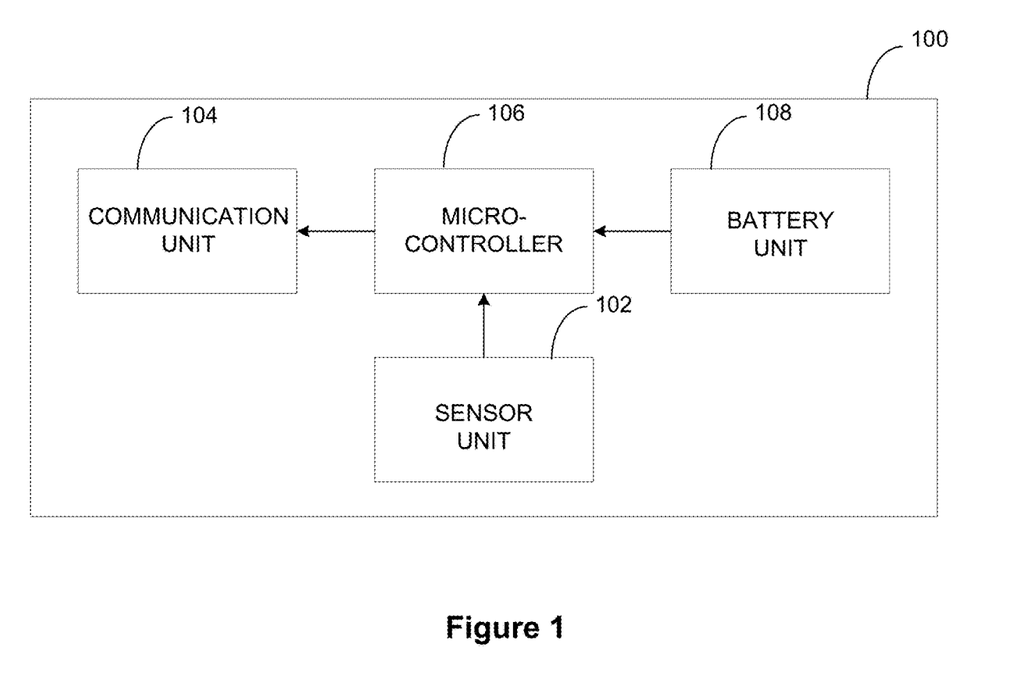
FIG. 1 is a block diagram of the components of a wireless mote according to an embodiment of the present invention.

Referring now to FIG. 1, a block diagram of the components of a wireless mote is shown. Wireless mote 100 includes a sensor unit 102, communication unit 104, microcontroller 106 and battery unit 108. Sensor unit 102 can be a volatile organic compound sensor configured to identify gas composition, gas concentration and complemented by relative humidity and temperature measurement. A volatile organic sensor is composed of a material that change resistance as methane molecules comes in contact with the surface resulting in a change of resistance. One such material can be SnO2-doped (tin dioxide) with transitional metals like Pd (palladium) or Pt (platinum) or any of the various other materials that have been demonstrated to be sensitive to methane detection. Communication unit 104 can be configured to transmit wireless data to a control server (not shown) and to receive wireless data from a control server, or in a wireless mesh network, communication unit can transmit wireless data or receive wireless data from another wireless mote in the wireless mesh network. Micro-controller 106 can be configured to manage the sampling rate of sensor unit 102 and transmission of data by communication unit 104. Battery unit 108 serves as a power supply to sensor unit 102, communication unit 104 and micro-controller 106. Battery unit 108 is a standard battery known in the art and may range in capacity from about 400 mAh to about 24000 mAh. In order to maximize the length of operation of wireless mote 100, sensor unit 102 consumes from about 10 μW to about 100 mW of power, communication unit 103 consumes from about 1 mW to about 1 W of power, and micro-controller 106 consumes from about 10 pW to about 3 mW of power. An advantage of using wireless mote 100 is that there is minimal burden to attach wires and power lines to sensing points, which is optimal if measurements are taken outdoors.

Figure 2:
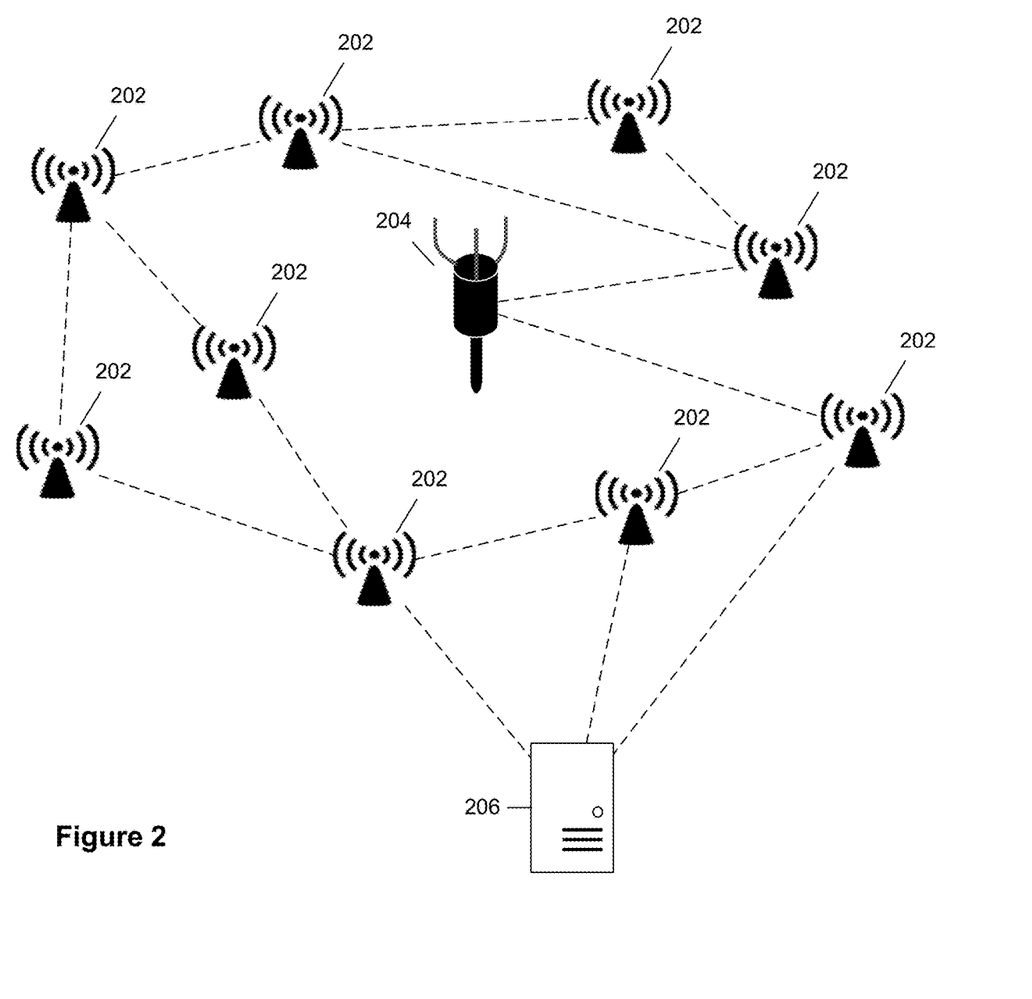
FIG. 2 is diagram of a system for adaptively sensing a gas leak according to an embodiment of the present invention.

FIG. 2 shows a diagram of a system for adaptively sensing a gas leak according to various embodiments of the present invention. Here, a plurality of wireless motes 202 (see FIG. 1) are arranged in order to encircle a gas extraction well pad where wind sensor 204 is centrally located. In other embodiments, wind sensor 204 can be located in order to maximize measurement of wind speed and wind direction. Wind sensor 204 should be configured to be as accurate as possible such that the accuracy of wind direction measurement should be within 1 to 2 degrees of the actual wind direction and the accuracy of wind speed measurement should be within 0.1 m/s of the actual wind speed.

In other embodiments of the present invention, there may be more than one wind sensor 204 located around the gas extraction well pad in order to maximize the accuracy of wind speed and wind direction measurements. The wind sensors may be configured to obtain sub-second measurements at a frequency from about 1 Hz to about 100 Hz in order to assess the autocorrelation of the wind speed and wind direction and understand the temporal stability of the wind conditions. The frequency at which the wind data is measured determines how quickly the wind changes direction on a local scale and its effect on the movement of the gas plume toward or away from a wireless mote.

The plurality of wireless motes 202 and wind sensor 204 can communicate via a wireless mesh network (dashed lines) that enables communication with control server 206. A wireless mesh network is a communications network made up of radio nodes organized in a mesh topology. A mesh topology refers to rich interconnection among devices or nodes. The coverage area of the radio nodes working as a single network is sometimes called a mesh cloud. Access to this mesh cloud is dependent on the radio nodes working in harmony with each other to create a radio network. A mesh network is reliable and offers redundancy. When one node can no longer operate, the rest of the nodes can still communicate with each other, directly or through one or more intermediate nodes. Wireless mesh networks can self-form and self-heal. Wireless mesh networks work with different wireless technologies including 802.11, 802.15, 802.16, cellular technologies and need not be restricted to any one technology or protocol. The use of a wireless mesh network ensures that data is not lost due to a non-functioning wireless mote, but also allows for a reduction in the number of wireless motes required to carry data to control server 206.

Control server 206 is a computer system/server, which is operational with numerous other general purpose or special purpose computing system environments or configurations. Examples of well-known computing systems, environments, and/or configurations that may be suitable for use with control server 206 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The components of control server 206 may include, but are not limited to, one or more processors or processing units (not shown), a system memory (not shown), and a bus (not shown) that couples various system components including system memory (not shown) to processor (not shown). Bus (not shown) represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Control server 206 typically includes a variety of computer system readable media. Such media may be any available media that is accessible by control server 206, and it includes both volatile and non-volatile media, removable and non-removable media. System memory (not shown) can include computer system readable media in the form of volatile memory, such as random access memory (RAM) (not shown) and/or cache memory (not shown). Control server 206 may further include other removable/non-removable, volatile/non-volatile computer system storage media. By way of example only, storage system (not shown) can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus (not shown) by one or more data media interfaces. As will be further depicted and described below, memory (not shown) may include at least one program product having a set (e.g., at least one) of program modules that are configured to carry out the functions of embodiments of the invention.

Program/utility (not shown), having a set (at least one) of program modules (not shown), may be stored in memory (not shown) by way of example, and not limitation, as well as an operating system, one or more application programs, other program modules, and program data. Each of the operating system, one or more application programs, other program modules, and program data or some combination thereof, may include an implementation of a networking environment. Program modules (not shown) generally carry out the functions and/or methodologies of embodiments of the invention as described herein.

Control server 206 may also communicate with one or more external devices (not shown) such as a keyboard, a pointing device, a display (not shown), etc.; one or more devices that enable a user to interact with computer system/server 12; and/or any devices (e.g., network card, modem, etc.) that enable computer system/server (not shown) to communicate with one or more other computing devices. Such communication can occur via Input/Output (I/O) interfaces (not shown). Still yet, control server 206 can communicate with one or more networks such as a local area network (LAN), a general wide area network (WAN), and/or a public network (e.g., the Internet) via network adapter (not shown). As depicted, network adapter (not shown) communicates with the other components of control server 206 via bus (not shown). It should be understood that although not shown, other hardware and/or software components could be used in conjunction with control server 206. Examples, include, but are not limited to: microcode, device drivers, redundant processing units, external disk drive arrays, RAID systems, tape drives, and data archival storage systems, etc.

Control server 206 can be configured to manage the plurality of wireless motes on the gas extraction well pad. The plurality of wireless motes may be in a "sleep mode" to preserve battery life. Control server 206 can send commands to activate or trigger measurement gathering on a single wireless mote, a subset of wireless motes or the plurality of wireless motes. In embodiments of the present invention, upon determination of wind speed and wind direction, control server 206 can send a command to trigger measurement gathering on a subset of wireless motes that are expected to detect the gas plume. The process of adaptive sensing is further detailed below in FIG. 3.

Figure 3:
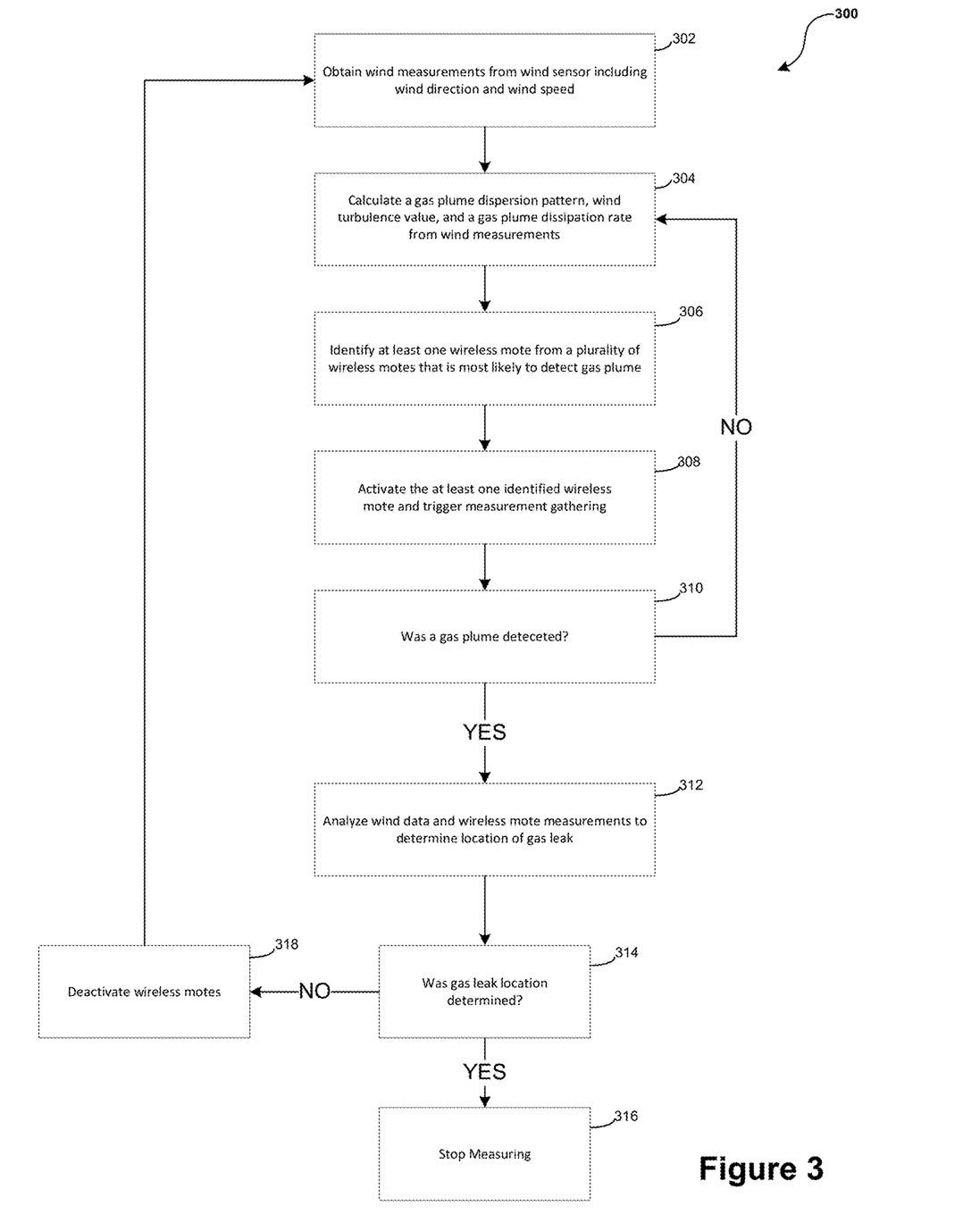
FIG. 3 is a flowchart of the process for adaptively sensing a gas leak according to an embodiment of the present invention.

Now referring to FIG. 3, a flowchart illustrating the process for adaptively sensing a gas leak is shown according to various embodiments of the present invention. In FIG. 3, process 300 starts at step 302 where wind measurements such as wind speed and wind direction are obtained from a wind sensor. At step 304, a gas plume dispersion pattern can be determined from the wind measurements, which is then used to determine a wind turbulence value. The gas plume dispersion pattern can indicate the proximity of the gas leak location in that if the leak is in close proximity then measurements would be very noisy with intermittent peak detection, whereas if the leak is farther away then there would be continuous, smooth detection. Once the wind turbulence value is calculated it can be used to determine a gas plume dissipation rate.

In order to determine the gas plume dispersion rate, the wind turbulence value and the gas plume dissipation rate, the modeling equations described below can be used. It should be noted that one of ordinary skill in the art may employ any modeling equations suitable for the intended purpose.

Plume Dispersion Equation $$C_{max} = \frac{Q}{\pi u \sigma_y \sigma_z} \exp\left(-\frac{1}{2}\frac{H^2}{\sigma_z^2}\right)$$

In the equation above, the $C_{max}$ is the maximum ground level concentration of gas emission at a point (x, y, z) measured in µg/m³. x is the meters downwind from the gas leak source (or emission source point). y is the meters crosswind from the gas plume centerline (or emission plume centerline). z is the meters above ground level.

Q is the gas emission rate in µg/s. $\sigma_y$ and $\sigma_z$ are the horizontal and vertical dispersion of gas emission, respectively, measured in meters.

u is the average wind speed at stack height in m/s.

H is the effective stack height, which is calculated by adding the plume rise in meters to the physical stack height in meters.

Furthermore, the equation above requires the plume rise, which can be determined using the following Briggs equation.

$$C_{x,y,z} = \frac{Q}{u} \cdot \frac{f}{\sigma_y \sqrt{2\pi}} \cdot \frac{g_1 + g_2 + g_3}{\sigma_z \sqrt{2\pi}}$$

In the equation above, C is the concentration of emissions, in g/m³, at any wireless mote location. x is the meters downwind from the gas leak source (or emission source point). y is the meters crosswind from the gas plume centerline (or emission plume centerline). z is the meters above ground level.

$f=\exp[-y^2/(2\sigma_y^2)]$, which is the crosswind dispersion parameter.

g is the vertical dispersion parameter, which is equal to $g_1+g_2+g_3$.

$g_1=\exp[-(z-H)^2/(2\sigma_z^2)]$, which is the vertical dispersion with no reflections.

$g_2=\exp[-(z+H)^2/(2\sigma_z^2)]$, which is the vertical dispersion for reflection from the ground.

$g_3=\Sigma_{m=1}^{\infty}\{\exp[-(z-H-2\ mL)^2/(2\sigma_z^2)]+\exp[-(z+H+2\ mL)^2/(2\sigma_z^2)]+\exp[-(z+H-2\ mL)^2/(2\sigma_z^2)]+\exp[-(z-H+2\ mL)^2/(2\sigma_z^2)]\}$, which is the vertical dispersion for reflection from an inversion aloft. L is the height from ground level to the bottom of the inversion aloft in meters. All other variables are the same as discussed above in the Gas Plume Dispersion Equation.

Using the wind turbulence value and gas plume dissipation rate, at step 306, at least one wireless mote in a plurality of wireless motes that is most likely to detect the presence of a gas plume is identified. Next, at step 308, the at least one identified wireless mote in the plurality of wireless motes is activated to begin gathering measurement data such as gas composition, gas concentration, temperature and relative humidity.

In an embodiment of the present invention, at step 308, the at least one identified wireless mote in the plurality of wireless motes is activated to begin gathering measurement data at an interval more frequent than the remaining wireless motes in the plurality of wireless motes.

In another embodiment of the present invention, at step 308, the at least one identified wireless mote in the plurality of wireless motes is activated to begin gathering measurement data at a well-defined moment of time when the gas plume is expected to pass nearby the at least one wireless mote, wherein the well-defined moment of time can be calculated using the wind turbulence value and the gas plume dispersion pattern. Also, the well-defined moment of time can be assumed to be the distance between the wireless mote and the source of the gas leak divided by the instantaneous wind speed value received from the wind sensor.

In another embodiment of the present invention, at step 308, if the location of the gas leak is already known, then the distance between the at least one wireless more in the plurality of wireless motes and the location of the gas leak can be calculated and the at least one identified wireless mote is activated to begin gathering measurement data at an interval proportional to a gas plume concentration and the calculated distance.

It is important to note that at step 308 less than all of the wireless motes available are activated. In various embodiments of the present invention, the remaining wireless motes in the plurality of wireless motes are excluded from taking measurements. Only those wireless motes that might be exposed to a gas plume are activated and required to take measurements, which extends battery lifetime and reduces the required data communication bandwidth. Furthermore, the power consumption of the sensor unit and communication unit (see FIG. 1) are reduced.

It should be understood that "activated" may mean any of the following: (1) being awakened from a "sleep mode", (2) triggered to acquire measurements at an interval much shorter (i.e., sample faster) than the wireless motes that are not "activated", or (3) any meaning that would be apparent to one of ordinary skill in the art in order to maximize the likelihood of gas plume detection.

At step 310, it is determined whether a gas plume is detected based on the measurement data acquired from the activated wireless motes at step 308. If a gas plume is detected then the process continues to step 312, otherwise the process returns to step 304. At step 312, the wind measurements and the measurements acquired at the activated wireless motes are analyzed to determine the location of the gas leak. The analysis is based on the back propagation of the wind direction while a methane peak is detected (see FIGS. 4(a)-4(d)). If a location is determined, then the escape rate of the gas plume can be calculated along with the chemical composition of the gas plume.

At step 314, if the location of the gas leak is determined, then the process proceeds to step 316 and measurement gathering is stopped. Alternatively, if the gas leak location cannot be determined at step 314, then the process continues to step 318 where all of the wireless motes are deactivated and the process restarts at 302. Process 300 can be performed recursively until the location of the gas leak is determined.

Furthermore, once process 300 has determined the location of the gas leak, additional analytics can be run by the activated wireless motes. For instance, the wireless motes can calculate the escape rate of the gas plume from the site of the gas leak and determine the chemical composition of the gas leak. As an example, the gas plume may be 80 percent methane and 20 percent ethane, which is information that could be important to one of ordinary skill in the art.

Figure 4A:
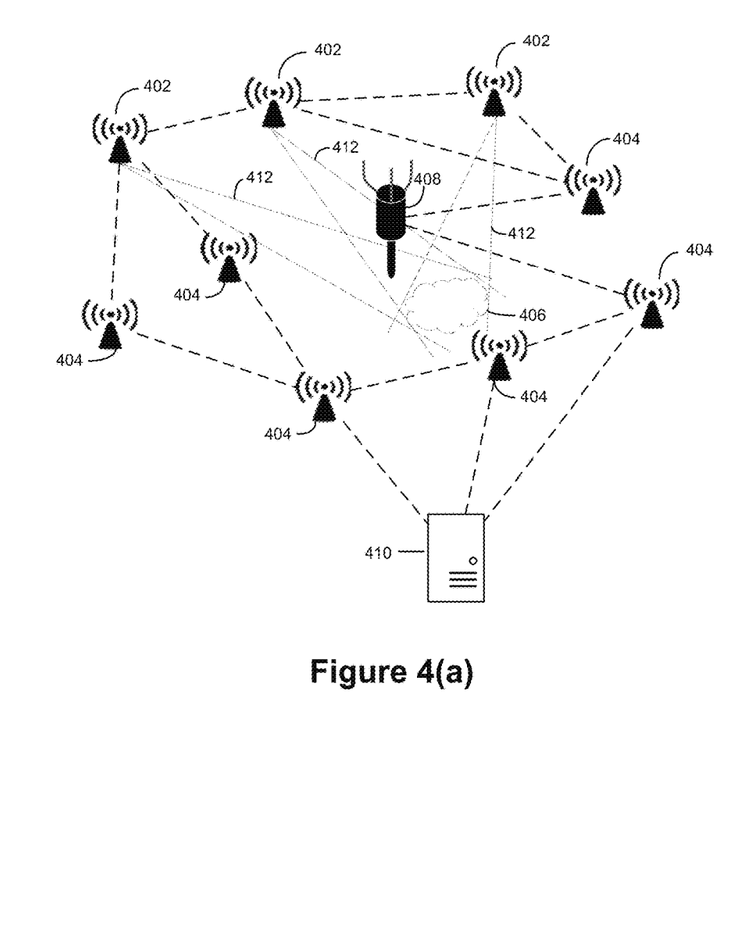
FIG. 4(a) is a diagram illustrating a system for adaptively sensing a gas leak according to an embodiment of the present invention.

In FIGS. 4(a)-4(d), an example of determining the location of a gas leak is illustrated. FIG. 4(a) shows a system for adaptively sensing a gas leak according to an embodiment of the present invention. In FIG. 4(a), wireless motes 402 are activated from the plurality of wireless motes and taking measurements of the environment in order to detect the possible gas leak 406. The remaining wireless motes 404 in the plurality of wireless motes are not activated and excluded from measurement gathering. Wind sensor 408 measures wind speed and wind direction and transmit the data to control server 410. Control server 410 can determine the location of possible gas leak 406 based on the measurements from wireless motes 402 and wind sensor 408, which is shown by projection lines 412.

Figure 4B:
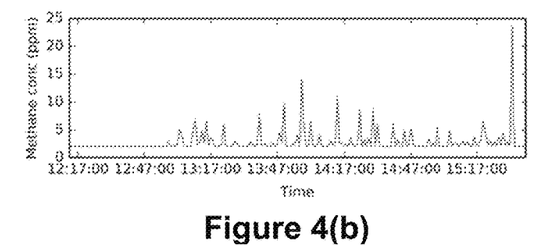
FIG. 4(b) is an example of a graph illustrating gas concentration data sent by a wireless mote according to an embodiment of the present invention.

In FIG. 4(b), an example of gas concentration data sent by an activated wireless mote is shown. Here, the detected concentration of methane in parts per million is plotted against the time the measurements were collected. In particular, the highest concentrations of methane were detected between 13:47 and 14:17.

Figure 4C:
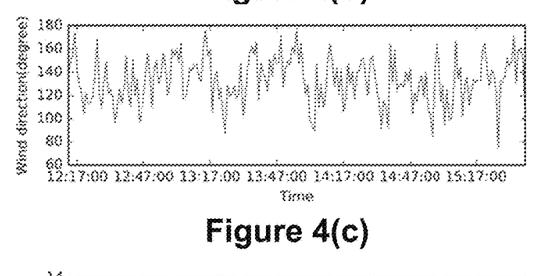
FIG. 4(c) is an example of a graph illustrating wind direction data sent by a wind sensor according to an embodiment of the present invention.

In FIG. 4(c), an example of wind direction data sent by a wind sensor is shown. Here, the wind direction is reported as degrees plotted against the time the measurements were collected. Here, the wind direction can be seen to change from 80 degrees to 180 degrees over time.

Figure 4D:
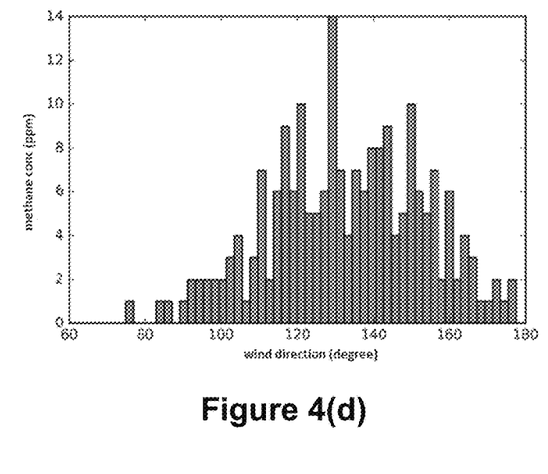
FIG. 4(d) is an example of a graph illustrating wind direction data corresponding to gas concentration data according to an embodiment of the present invention.

In FIG. 4(d), an example of a graph of the gas concentration data of FIG. 4(b) plotted against the wind direction data of FIG. 4(c). Here, it can be seen that the highest concentration of methane is observed when the wind direction is between 120 and 140 degrees. Using this graphical information for each activated wireless mote 402, the projection lines 412 of FIG. 4(a) can be determined.

Figure 5:
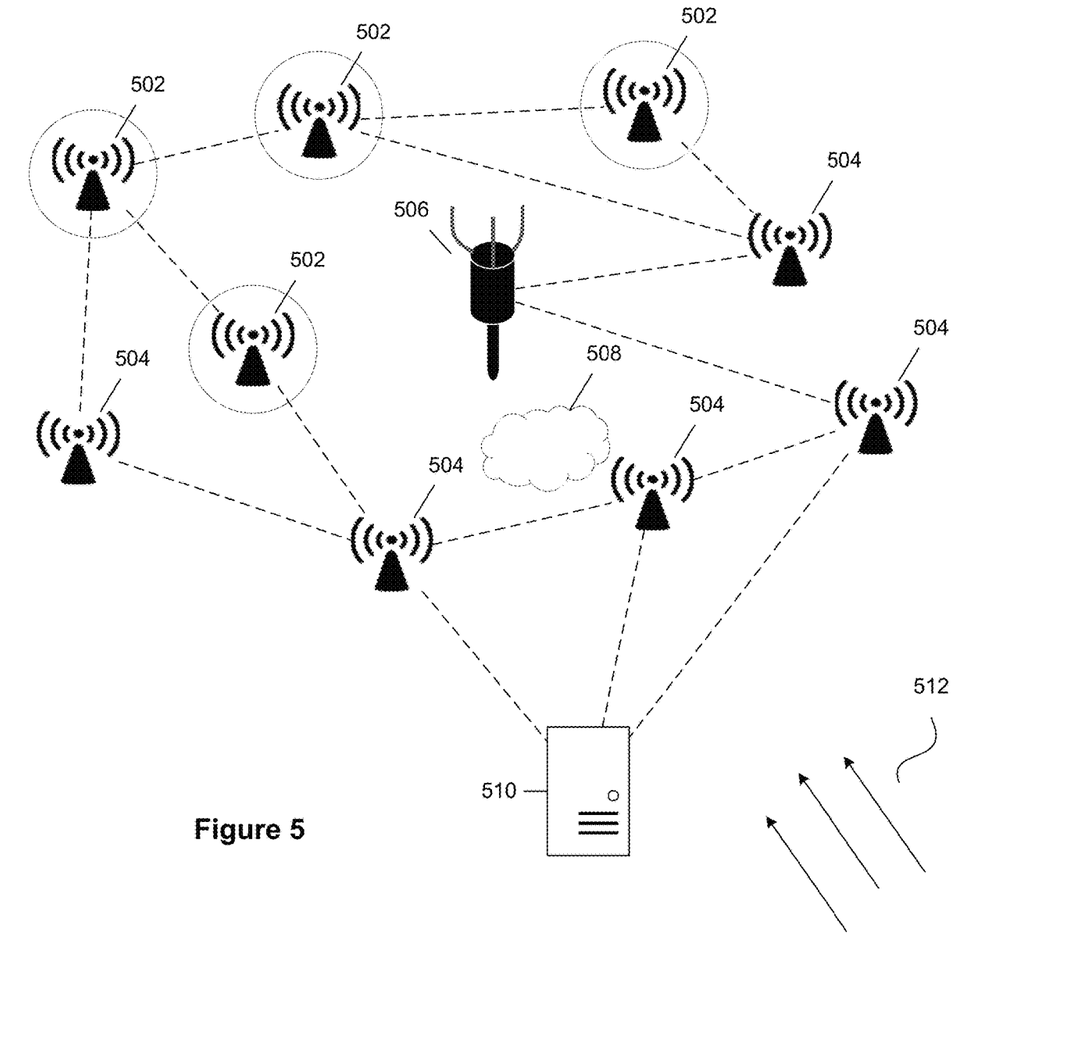
FIG. 5 is a diagram illustrating a system for adaptively sensing a gas leak according to an embodiment of the present invention.

Referring to FIG. 5, a system for adaptively sensing a gas leak is shown according to various embodiments of the present invention. In FIG. 5, wireless motes 502 are encircled to show that they are activated from the plurality of wireless motes and taking measurements of the environment in order to detect the gas leak 508. The remaining wireless motes 504 in the plurality of wireless motes are not activated and excluded from measurement gathering. Wireless motes 502 are activated by control server 510 based on the measurements taken from wind sensor 506, which is represented by wind direction arrows 512.

In this embodiment, it can be seen that wind direction arrows 512 will move gas leak 508 into the path of activated wireless motes 502. Consequently, control server 510 will not send an activation command to the remaining wireless motes 504 in the plurality of wireless motes as they will not detect gas leak 508. Furthermore, activated wireless motes 502 send real-time measurement data to the control server 510 such that gas plume models can be developed using the real-time measurement data. The gas plume models can determine the relative size of the gas plume and predict the movement of the gas plume, which enables identification of which wireless motes in the plurality of wireless motes should be activated.

Wind sensor 508 continuously provides wind speed and wind direction measurements to control server 510 such that wind direction arrows 512 will vary direction based on the wind conditions resulting in the possibility wireless motes in the remaining wireless motes 504 in the plurality of wireless will be activated to take measurements, while the currently activated wireless motes 502 will be deactivated since they will no longer be in the path of gas leak 508.

Figure 6:
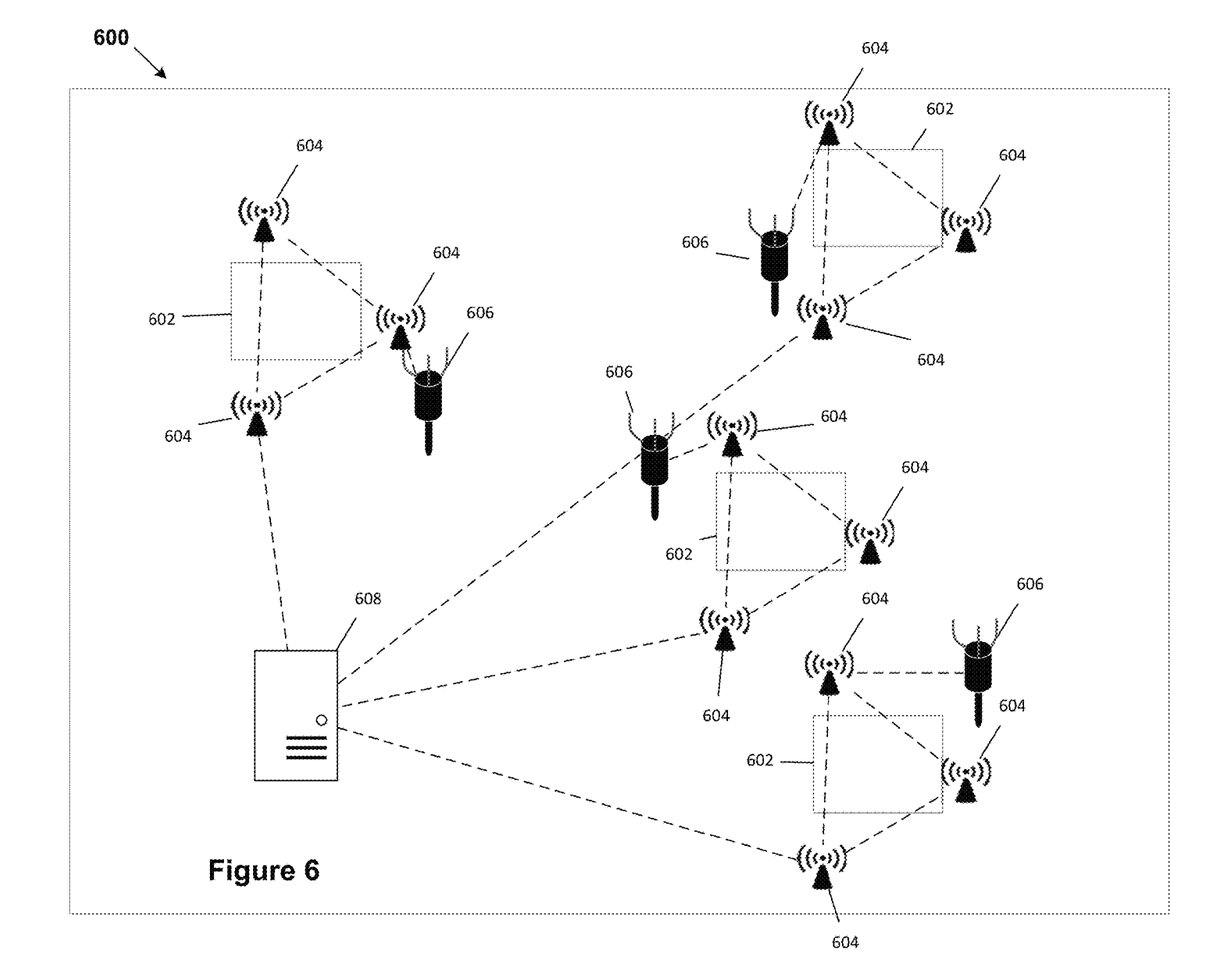
FIG. 6 is a diagram illustrating a system for adaptively sensing a gas leak in an industrial site having multiple gas extraction well pads according to an embodiment of the present invention.

Referring to FIG. 6, a system for adaptively sensing a gas leak in an industrial site having multiple gas extraction well pads is shown according to an embodiment of the present invention. Here, industrial site 600 can have a plurality of gas extraction well pads 602 and at each gas extraction well pad there can be a plurality of wireless motes 604 and wind sensors 606 that can communicate with control server 608. At each gas extraction well pad exists a system for adaptively sensing a gas leak as discussed in FIG. 2 above. In this embodiment, a potential gas leak at any individual gas extraction well pad 602 can be sensed by either the system of the individual gas extraction well pad or an adjacent gas extraction well pad, or a combination thereof.

Control server 608 can activate wireless motes 604 based on the wind speed and wind direction measurements from any individual wind sensor 606, or a collection of measurements from a subset of wind sensors 606, or the plurality of wind sensors 606. In addition, the wind sensor 606 providing the wind speed and wind direction measurements is not required to be located on the same gas extraction well pad 602 as the wireless motes 604 to be activated.

The system can be used to adaptively sense the environment when one single gas leak is present on a gas extraction well pad or when there are multiple leaks present. Alternatively, the system can be used to sense gas leaks on a gas extraction well pad in the surrounding area. In case of multiple leaks on a gas extraction well pad, multiple gas plumes may be dispersed across the gas extraction well pad that requires complex analytics based on mixing gas plume models to determine which wireless mote(s) may fall within the range of the gas leaks.

Also, in a situation where multiple gas extraction well pads are in close proximity, the gas extraction well pads may have a wireless sensor network covering multiple gas extraction well pads. For a large area, the wind may carry a gas plume from one gas extraction well pad to another gas extraction well pad that is nearby. In this case, control server 608 may activate wireless motes 604 on multiple gas extraction well pads. The communication between gas extraction well pads 602 are bidirectional such that information can be sent and received.

System 600 can integrate short term weather forecast, such as provided by the Weather Channel, such that wind speed and wind direction predictions can be integrated into the system to forecast which wireless motes 604 should be activated to sense a gas plume.

What is claimed is:

1. A method of adaptively sensing a gas leak, the method comprising:
   obtaining first wind data from a wind sensor, the first wind data comprising a wind speed and a wind direction;
   identifying a first wireless mote in a plurality of wireless motes that is in a path of the gas leak based on the first wind data, wherein the plurality of wireless motes comprises a second wireless mote that is not in the path of the gas leak;
   selectively activating the identified first wireless mote to trigger measuring a gas concentration of a gas plume, wherein the second wireless mote is not activated;
   comparing the measured gas concentration to a predetermined threshold; and
   identifying a location of the gas leak.

2. The method according to claim 1, further comprising:
   obtaining second wind data from the wind sensor in response to the gas concentration being below the predetermined threshold;
   identifying a third wireless mote in the plurality of wireless motes that is in the path of the gas leak based on the second wind data; and
   selectively activating the identified third wireless mote to trigger measuring a gas concentration of the gas plume.

3. The method according to claim 1, wherein identifying the first wireless mote in the plurality of wireless motes comprises:
   calculating a wind turbulence value from the wind data and the gas plume dispersion pattern;
   calculating a gas plume dissipation rate from the wind turbulence value; and
   identifying the at least one wireless mote in the plurality of wireless motes that is in a path of the gas plume from the wind turbulence and the gas plume dissipation rate.

4. The method according to claim 1, further comprising:
   measuring the gas concentration at the identified first wireless mote more frequently than at the second wireless mote.

5. The method according to claim 4, further comprising:
   excluding the second wireless mote in the plurality of wireless motes from taking measurements to conserve power and data communication bandwidth.

6. The method according to claim 1, further comprising:
   calculating a well-defined moment of time when the gas plume is expected to pass near the identified first wireless mote, wherein the well-defined moment of time is determined based on a distance between the first wireless mote and a source of the gas leak divided by the wind speed of the first wind data received from the wind sensor; and
   measuring gas concentration at the well-defined moment of time.

7. The method according to claim 1, further comprising:
   identifying gas type, relative humidity and temperature.

8. The method according to claim 1, further comprising:
   calculating an escape rate of the gas plume from the gas leak; and
   determining the chemical composition of the gas plume.

9. A system for adaptively sensing a gas leak, comprising:
   a wind sensor located on a gas extraction well pad, wherein the wind sensor is configured to obtain wind data by sensing wind speed and wind direction;
   a plurality of wireless motes located in proximity of the wind sensor, wherein each wireless mote is configured to detect the presence of gas; and
   a server located in proximity of the gas extraction well pad, wherein the server is configured to communicate with the plurality of wireless motes and the wind sensor; wherein the server is further configured to:
   identify a first wireless mote in the plurality of wireless motes that is in a path of the gas leak based on the wind data, wherein the plurality of wireless motes comprises a second wireless mote that is not in the path of the gas leak; and
   selectively activate the identified first wireless mote to trigger measuring a gas concentration of a gas plume, wherein the second wireless mote is not activated.

10. The system according to claim 9, wherein the server is further configured to:
    activate a first wireless mote in the plurality of wireless motes to take a measurement at an interval more frequent than for a second wireless mote in the plurality of wireless motes.

11. The system according to claim 10, wherein the server is further configured to:
    exclude at least one wireless mote in the plurality of wireless motes from taking measurements to conserve power and data communication bandwidth.

12. The system according to claim 10, wherein the server is further configured to:
    calculate a well-defined moment of time when the gas plume is expected to pass near the identified first wireless mote, wherein the well-defined moment of time is determined based on a distance between the first wireless mote and a source of the gas leak divided by the wind speed received from the wind sensor; and measure gas concentration at the well-defined moment of time.

13. The system according to claim 12, wherein the server is further configured to:
determine a location of the gas leak using the wind data and the gas measurement from the first wireless mote in the plurality of wireless motes.

14. The system according to claim 9, wherein the server is further configured to:
calculate an escape rate of the gas plume from the gas leak; and
determine the chemical composition of the gas plume.

15. A system for adaptively sensing a gas leak in an industrial site, comprising:
a plurality of gas extraction well pads contained in the industrial site;
a plurality of wind sensors each located in the proximity of each gas extraction well pad, wherein each wind sensor is configured to obtain wind data by sensing wind speed and wind direction;
a plurality of wireless motes located in the proximity of each gas extraction well pad and a wind sensor in plurality of wind sensors, wherein each wireless mote is configured to detect the presence of gas; and
a server located in proximity of the industrial site, wherein the server is configured to communicate with the plurality of wireless motes and the plurality of wind sensors; wherein the server is further configured to:
identify a first wireless mote in the plurality of wireless motes that is in a path of the gas leak based on the wind data, wherein the plurality of wireless motes comprises a second wireless mote that is not in the path of the gas leak; and
selectively activate the identified first wireless mote to trigger measuring a gas concentration of a gas plume, wherein the second wireless mote is not activated.

* * * * *